United States Patent
Fischer et al.

(10) Patent No.: US 10,390,725 B2
(45) Date of Patent: Aug. 27, 2019

(54) CONNECTION OF COILS TO AN MR DEVICE

(71) Applicants: Hubertus Fischer, Bamberg (DE); Katharina Hesels, Erlangen (DE); Karsten Jahns, Buckenhof (DE); Wolfgang Kraus, Fürth (DE); Thomas Kundner, Buckenhof (DE); Steffen Wolf, Röttenbach (DE); Jörg Rothard, Litzendorf (DE)

(72) Inventors: Hubertus Fischer, Bamberg (DE); Katharina Hesels, Erlangen (DE); Karsten Jahns, Buckenhof (DE); Wolfgang Kraus, Fürth (DE); Thomas Kundner, Buckenhof (DE); Steffen Wolf, Röttenbach (DE); Jörg Rothard, Litzendorf (DE)

(73) Assignee: Siemens Aktiengesellschaft, München (DE)

(*) Notice: Subject to any disclaimer, the term of this patent is extended or adjusted under 35 U.S.C. 154(b) by 776 days.

(21) Appl. No.: 15/044,757

(22) Filed: Feb. 16, 2016

(65) Prior Publication Data
US 2016/0238677 A1 Aug. 18, 2016

(30) Foreign Application Priority Data

Feb. 17, 2015 (DE) .................. 10 2015 202 793
Feb. 17, 2015 (DE) .................. 10 2015 202 795

(51) Int. Cl.
*A61B 5/00* (2006.01)
*A61B 5/055* (2006.01)
(Continued)

(52) U.S. Cl.
CPC .......... *A61B 5/055* (2013.01); *G01R 33/3415* (2013.01); *G01R 33/36* (2013.01); *G01R 33/34007* (2013.01)

(58) Field of Classification Search
CPC .... A61B 5/055; G01R 33/36; G01R 33/3415; G01R 33/34007
See application file for complete search history.

(56) References Cited

U.S. PATENT DOCUMENTS 6,134,465 A 10/2000 Frederick et al.
6,134,665 A 10/2000 Klein et al.
(Continued)

FOREIGN PATENT DOCUMENTS

CN 105891751 A 8/2016
DE 102009018608 A1 11/2010
(Continued)

OTHER PUBLICATIONS

Korean Office Action for related Korean Application No. 9-5-2017-055173690 dated Aug. 8, 2017.
(Continued)

*Primary Examiner* — Joel Lamprecht
(74) *Attorney, Agent, or Firm* — Lempia Summerfield Katz LLC (57) ABSTRACT

An accessory comprises at least one first electrical accessory port for connection to a respective matching electrical coil port of an MR coil and at least one second electrical accessory port for connection to a respective matching electrical device port of an MR device. The first accessory port and the second accessory port do not match one another. The respective first accessory port is connected to the associated second accessory port by electrical adaptation.

9 Claims, 5 Drawing Sheets (51) Int. Cl.
    *G01R 33/3415*      (2006.01)
    *G01R 33/36*      (2006.01)
    *G01R 33/34*      (2006.01)

(56)      References Cited

U.S. PATENT DOCUMENTS

| | | |
|---|---|---|
| 6,362,622 B1 | 3/2002 | Stauber et al. |
| 7,345,485 B2 | 3/2008 | Jevtic et al. |
| 8,487,619 B2 * | 7/2013 | Biber ............... G01R 33/34007 324/307 |
| 2010/0271027 A1 | 10/2010 | Biber et al. |
| 2016/0238677 A1 | 8/2016 | Fischer et al. |

FOREIGN PATENT DOCUMENTS

| | | | |
|---|---|---|---|
| JP | 2000083923 A | 3/2000 | |
| JP | 2001346775 A | 12/2001 | |
| JP | 2014213084 A | 11/2014 | |
| KR | 20160101698 A | 8/2016 | |

OTHER PUBLICATIONS

Korean Office Action for related Korean Application No. 10-2016-0017923 dated Apr. 13, 2017, with English Translation.
German Office action for related German Application No. 10 2015 202 795.3, dated Jan. 26, 2016, with English Translation.
Chinese Office Action for Chinese Application No. 201610086046.9 dated Mar. 30, 2018, with English Translation.

\* cited by examiner

CONNECTION OF COILS TO AN MR DEVICE

This application claims the benefit of DE 10 2015 20 2795.3, filed on Feb. 17, 2015, and DE 10 2015 20 2793.7 filed on Feb. 17, 2015, which are hereby incorporated by reference in their entirety.

TECHNICAL FIELD

The embodiments relate to a magnetic resonance tomography device.

BACKGROUND

Typically, MR surface coils that are conformable and can be positioned or placed flexibly on the patient are used for imaging examinations using magnetic resonance tomography of body regions such as, for example, the upper body, the abdomen, the liver, the heart, the pelvis or prostate. Here, the aim is to obtain images with the greatest possible image quality with the shortest possible examination period. The short examination time is particularly advantageous in order to reduce the influence of artifacts in motion-sensitive examinations.

For the aforementioned MR examinations, it is possible to place MR surface coils as local coils both beneath the patient ("posteriorly") and on the patient ("anteriorly") to acquire signals simultaneously during the MR measurement.

However, to date, these MR examinations have required the use of a combination of two different MR surface coils since there are no MR surface coils that can be used both anteriorly and posteriorly. One problem with this is that the MR surface coil has to be assigned different operating and/or evaluation parameters (so-called "coil file parameters") in the two different positions in order to achieve the best possible image quality. Moreover, the MR surface coils for anterior and posterior arrangement have coil cables of different lengths or no coil cables. To date, there have been two different arrangements for these MR examinations.

On the one hand, the examinations are performed using a combination of precisely one posterior MR surface coil (a so-called "spine coil") and an anterior 18-channel MR surface coil (a so-called "body coil"). However, to date, this combination includes a comparatively low number of coil elements in the MR surface coils resulting in a correspondingly lengthy measuring time. Moreover, this combination only achieves low coverage in the longitudinal direction or z direction of the patient.

On the other hand, the examinations can be performed with a coil set made by the company Invivo. In this case, one MR surface coil is positioned anteriorly and another MR surface coil positioned posteriorly. However, the two MR surface coils have different cable lengths and hence require different material numbers. In addition, these MR surface coils are frequently associated with an excessively long measuring time.

SUMMARY AND DESCRIPTION

The scope of the present invention is defined solely by the appended claims and is not affected to any degree by the statements within this summary The present embodiments may obviate one or more of the drawbacks or limitations in the related art Embodiments relate to an accessory for a magnetic resonance tomography (MR or MRT) device. Embodiments further relate to an MR device including a patient bed with at least one first device port for connecting an anteriorly positioned MR coil and with at least one second device port for connecting a posteriorly positioned MR coil and including a memory that stores at least one set of coil file parameters for the anteriorly positioned MR coil and one set of coil file parameters for the posteriorly positioned MR coil. The two device ports are designed differently. Embodiments also relate to an MR System including an MR device, a posteriorly arranged MR coil that is a surface coil with a plurality of coil elements and to which the at least one coil port is connected, and an anteriorly arranged MR coil that is a surface coil with a plurality of coil elements and the at least one coil port is connected to a respective first device port of the MR device. Embodiments also relate to a method for preparing an MR device with which the at least one coil port of an anteriorly arranged MR coil is connected to a respective first device port of the MR device. Embodiment are, for example, advantageously applicable to magnetic resonance tomography examinations of body regions such as the upper body, the abdomen, the liver, the heart, the pelvis or the prostate.

It is the object of the present invention to overcome the disadvantages of the state of the art. This object is achieved in accordance with the features of the independent claims.

The object is achieved by an accessory including at least one first electrical port (hereinafter called the first "accessory port" without restricting the generality) for connection to a respective matching electrical port (hereinafter called the "coil port" without restricting the generality) of an MR coil and at least one second electrical port (hereinafter called the second "accessory port" without restricting the generality) for connection to a respective matching electrical port (hereinafter called the "device port" without restricting the generality) of an MR device, wherein the first accessory port and the second accessory port do not match one another and a respective first accessory port is connected to an associated second accessory port by electrical adaptation or conversion.

This enables an MR coil to be connected to at least one device port of the MR device that is not per se suitable for the port of this coil. This enables the same MR coils to be optionally connected to different, non-matching device ports of the MR device, for example, for an MR coil to be arranged anteriorly or for an MR coil to be arranged posteriorly. The same MR coil with the same material number may be used for both the anterior arrangement and for the posterior arrangement, thus reducing costs for coil production, coil development, production support and in service.

The electrical port may include one or more electrical contact or poles and may be multi-polar.

The fact that a respective first accessory port may be connected to an associated second accessory port by electrical adaptation, may, for example, mean that a pin configuration of electrical contacts of the first accessory port is converted to a pin configuration of electrical contacts of the second accessory port or vice versa and with identical functions. Conversion with identical functions may, for example, be understood to mean that a function of the MR coil is not restricted by an interposition of the accessory or is retained to its full extent. If, for example, the first accessory port and the second accessory port have the same number of contacts, the accessory may convert a one-to-one electrical connection of the contacts of the first accessory port to the contacts of the associated second accessory port.

Adaptation in the accessory may be purely electrical conversion purely by wiring or may also be electronic conversion, for example, by the interposition at least one electronic component.

The accessory may also be referred to as an adapter, converter or an interface between an MR coil and an associated MR device or a part thereof. The accessory may also be referred to as an accessory part.

In one embodiment, the accessory includes at least two first accessory ports and at least two second accessory ports. This enables MR coils to be connected to a particularly high number of coil elements since the associated MR signals may be transmitted via more than one port.

In an embodiment, the at least one first accessory port is a manually pluggable part and the at least one second accessory port is a directly pluggable part. The manually pluggable part may be a plug, a socket or a combination thereof. The directly pluggable part may be a plug, a socket or a combination thereof.

In one embodiment, the MR coil is a surface coil with a plurality of coil elements. The MR surface coil may, for example, be positioned conformably and flexibly on the patient on or under the patient. The MR surface coil is, for example, embodied in a mat or cover shape. The at least one coil element may, for example, be a pure receive coil or only used as a receive coil. Alternatively, the at least one coil element may be a combined transmit/receive coil or used as such.

The MR coil may be positioned both anteriorly and posteriorly with respect to a patient.

In a further embodiment, the MR coil includes precisely two coil ports for connecting the coil elements. This enables the MR coils to be equipped with a particularly high number of coil elements and still connected in a simple manner.

For example, if the at least one coil port of the MR coil is equipped with or connected to a cable, it is particularly easy to displace a posteriorly arranged MR coil or to reposition it posteriorly.

In one development, the MR coil includes at least one coil element, at least one coil port to connect the at least one coil element to an MR device and at least one memory to store readable data. The memory is readable via the at least one coil port. This MR coil has the advantage that the coil is easy to identify and/or may hold information on operating parameters. The memory may be an electronic memory, an RFID, an electrical or electronic circuit among others.

The readable data may for example include one or more sets of coil file parameters. Alternatively or additionally, it is possible to read an identification or ID from the MR coil that uniquely identifies the type of coil. The identification may, for example, correspond to a specific material number or group of material numbers.

The object is also achieved by an MR device with at least one first device port for connecting a first MR coil and with at least one second device port for connecting a second MR coil and including a memory in which at least one set of coil file parameters is stored for the anteriorly positioned MR coil and one set of coil file parameters for the posteriorly positioned MR coil. The two device ports are designed differently, and the MR device is configured to read an identification of the anteriorly positioned MR coil via the first device port and an identification of the posteriorly positioned MR coil via the second device port, The MR device is configured to process MR signals originating from the anteriorly positioned MR coil using a set of coil file parameters, that are selected on the basis of the identification read from the anteriorly positioned MR coil and the connection of the anteriorly positioned MR coil to the first device port. The MR device is configured to process MR signals originating from the posteriorly positioned MR coil using a set of coil file parameters, which are selected on the basis of the identification read from the posteriorly positioned MR coil and the (also indirect) connection of the posteriorly positioned MR coil to the second device port.

This MR device has the advantage that the MR device may automatically assign the correct set of coil file parameters to a connected MR coil. In addition, the coil file parameters may be simply adapted using an update on the MR device. The actual MR coils do not have to be changed for this.

The MR device may, for example, be a patient bed or include a patient bed.

The fact that the MR device is configured to process MR signals originating from an MR coil using a matching set of coil file parameters, that are selected or determined on the basis of the identification read from the MR coil and the selected device port of the MR coil, may for example entail the fact that the MR device identifies which type of MR coil is connected to which device port and correspondingly selects or determines a suitable set of coil file parameters for this configuration.

The MR device may, for example, be a patient bed with at least one first device port for connecting a anteriorly positioned MR coil and with at least one second device port for connecting a posteriorly positioned MR coil. The MR device, is configured to identify the device port that the respective MR coil is connected, to read an identification of the MR coil via this device port and, by linking the device port with identification read therefrom, to determine the valid set of coil file parameters for this MR coil and for this device port. For example, the selected device port may indicate a specific position and/or usage of the MR coil, possibly in dependence on the identification of the MR coil. For example, a port of a specific type of MR coil that is uniquely identifiable by the identification at the first device port may indicate its anterior position and/or its use for an examination of the upper body, the abdomen, the liver, of the heart, the pelvis or the prostate.

The MR device may also include, for example, an MR tube with at least one transmit coil or "body coil" that the patient bed may be pushed into.

The object is also achieved by an MR System including an MR device as described above, an accessory as described above, the at least one second accessory port that is connected to the at least one second device port of the MR device, a posteriorly arranged MR coil that is a surface coil with a plurality of coil elements and at least one coil port that is connected to a respective first accessory port of the accessory and an anteriorly arranged, MR coil, that has the same design as the posteriorly arranged MR coil and the at least one coil port that is connected to a respective first device port of the MR device. The MR system may have a similar design to that of the MR device, the accessory and/or the MR coil and achieve the same advantages.

In particular, the MR System may include: a patient bed, an accessory connected by two plugs to two second device ports of the patient bed, a posteriorly arranged MR surface coil connected by two manually pluggable parts to two pluggable counterparts of the accessory, and an anteriorly arranged MR surface coil connected by two manually pluggable parts to a respective pluggable counterpart of the accessory.

In yet a further embodiment, the posteriorly positioned MR coil lies on a base that may be variably positioned on the patient bed in the longitudinal direction of the patient (and hence, as a rule, also in a longitudinal direction of the patient bed). This variable positioning may include a continuous and/or successive change to the position. For example, the base may be embodied as a coil slide that may be displaced relative to the patient bed. To this end, the patient bed may have one or more longitudinal guides as slide guides.

In yet a further embodiment, the MR device includes a positioning cushion set that enables a user of the MR device to displace the posteriorly positioned MR coil in a further region over the length of the bed, for example, over virtually the entire length of the bed. To this end, the positioning cushion set may for example include a plurality of segments that may be inserted in the patient bed in series along the length of the bed. The individual segments may then be selected for insertion in the patient bed such that they assume the desired length. If the base for the posteriorly positioned MR coil is displaced, segments may be removed or additionally inserted.

The object is also achieved by a method for preparing an MR device wherein the at least one second accessory port of the accessory is connected to the at least one second device port of a patient bed of the MR device, a posteriorly arranged MR coil at least one coil port that is connected to a respective first accessory port of the accessory and an anteriorly arranged MR coil at least one coil port that is connected to a respective first device port of the MR device.

The method may be embodied similarly to the above devices and achieve the same advantages.

For example, in one development, the MR device reads an associated identification from both the anteriorly arranged MR coil and from the posteriorly arranged MR coil and processes MR signals originating from the MR coils using a respective set of coil file parameters. The respective set of coil file parameters is selected on the basis of the identification read from the respective MR coil and of the connection of the respective MR coil to the respective device port identified by the MR device.

The scope of the present invention is defined solely by the appended claims and is not affected to any degree by the statements within this summary The above-described properties, features and advantages of this invention and also the manner in which these are achieved will become clearer and more plainly comprehensible in conjunction with the following schematic description of an exemplary embodiment explained in more detail in conjunction with the drawings. Here, for purposes of clarity, the same reference characters may be used for the same or similarly functioning elements.

DETAILED DESCRIPTION

Figure 1:
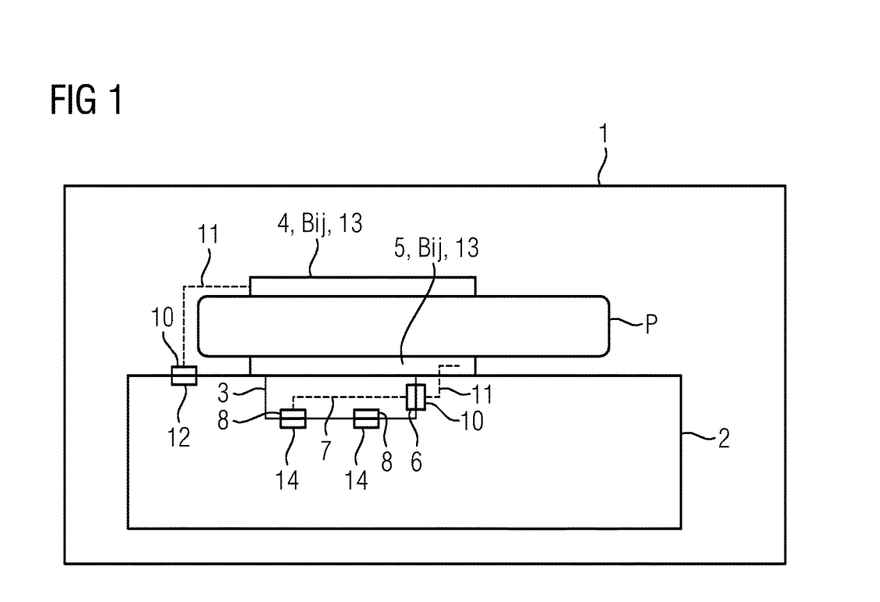
FIG. 1 depicts a side view of a sketch of an MR system according to an embodiment.

FIG. 1 depicts an MR System 1 including an MR device 2, 20 with a patient bed 2, an accessory 3 connected to the patient bed 2, an MR surface coil 4 arranged anteriorly to a patient P and an MR surface coil 5 arranged posteriorly to a patient P.

The accessory 3 includes two first electrical accessory ports. Only one first accessory port is shown here in the form of a socket 6. Each of the two sockets 6 is connected via wiring 7 to a respective second electrical accessory port in the form of a direct plug connector 8 by adaptation or conversion. The direct plug connector 8 is not designed to fit in the socket 6.

The two MR surface coils 4 and 5 have the same design and may have the same material number. The two MR surface coils 4 and 5 only differ in their positioning with respect to the patient P. The two MR surface coils 4 and 5 each include a plurality of coil elements Bij as shown in more detail in FIG. 3. The two MR surface coils 4 and 5 each also include two coil ports in the form of manual plugs 10. The manual plug connectors 10 are attached to a respective cable 11 or include a cable 11.

The manual plug connectors 10 of the anteriorly arranged MR surface coil 4 are inserted in respective sockets 12 of the patient bed 2 serving as first device ports, wherein the sockets 12 and the sockets 6 of the accessory 3 have the same design. The manual plug connectors 10 of the posteriorly arranged MR surface coil 5 are inserted in a respective socket 6 of the accessory 3. Therefore, in principle, the MR surface coils 4 and 5 may both be optionally inserted in either the patient bed 2 or the accessory 3.

The direct plug connector 8 of the accessory 3 is in each case inserted in a matching directly pluggable counter element 14 of the patient bed 2 serving as second device ports ("direct connect"). Therefore, the accessory 3 serves as an adapter or converter between the posteriorly positioned MR surface coil 5 and the patient bed 2. Due to the fact that, contrary to the otherwise usual directly plugged coils, the MR surface coil 5 includes a cable 11, the MR surface coil 5 may be displaced variably along a longitudinal body axis or z-axis of the patient P without any further preparation and together with the anteriorly positioned MR surface coil 4.

Each of the MR surface coils 4 and 5 further includes a memory 13 that may be read via the manual plug connector 10 and that stores the coils identification. The identification may correspond to a material number. Here, the identifications of the MR surface coils 4 and 5 are the same. The MR System 1 reads the identification for the anteriorly positioned MR surface coil 4 via the sockets 12 and the identification for the posteriorly positioned MR surface coil 5 via its directly pluggable counter elements 14. With knowledge of the identification and the electrical connection 12 or 14 used, the MR System is able to determine the set of coil file parameters suitable for the respective MR surface coils 4 or 5 and use it for processing the corresponding MR signals, for example, for imaging.

The MR signals received from the coil elements Bij of the anteriorly positioned MR surface coil 4 are, therefore, transmitted via the interface 'manual plug connector 10—socket 12' to the MR device 2, where the MR signals are, for example, used in an evaluation device for imaging corresponding body regions and using the previously determined coil file parameters. On the other hand, the MR signals received by the coil elements of the posteriorly positioned MR surface coil 5 are only transmitted via the interface (manual plug connector 10—socket 6) to the accessory 3, guided in the accessory 3 using the wiring 7 and transmitted using the interface (direct plug connector 8—directly pluggable counter element 14) to the MR device 2, where the MR signals may also be used, for example in an evaluation device for imaging corresponding body regions and using the previously determined coil file parameters.

Figure 2:
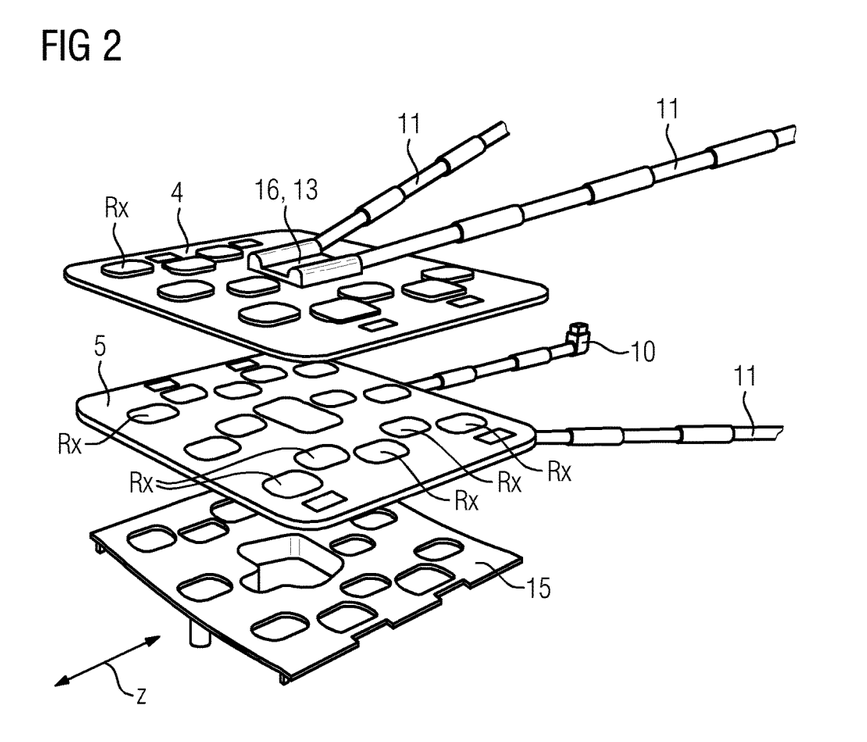
FIG. 2 depicts an anteriorly arranged MR surface coil, a posteriorly arranged MR surface coil, and a coil slide, according to an embodiment.

FIG. 2 is an oblique view of the anteriorly arranged MR surface coil 4 and the posteriorly arranged MR surface coil 5 without the patient located therebetween. FIG. 2 further shows beneath the MR surface coil 5, a coil slide 15 that may be displaced in the longitudinal direction or in z direction so that the position of the posteriorly arranged MR surface coil 5 lying thereupon may be varied correspondingly. This enables the posteriorly arranged MR surface coil 5 to be placed centrally on the patient bed 2 using simple means.

The two identically designed MR surface coils 4 and 5 each have a mat-, cover- or location-shaped basic shape that may be configured to the contours of the patient. The coil elements Bij are arranged in a regular (here: level, hexagonally tightly packed) basic pattern in the MR surface coils 4 and 5, as is explained in more detail in FIG. 3.

Figure 3:
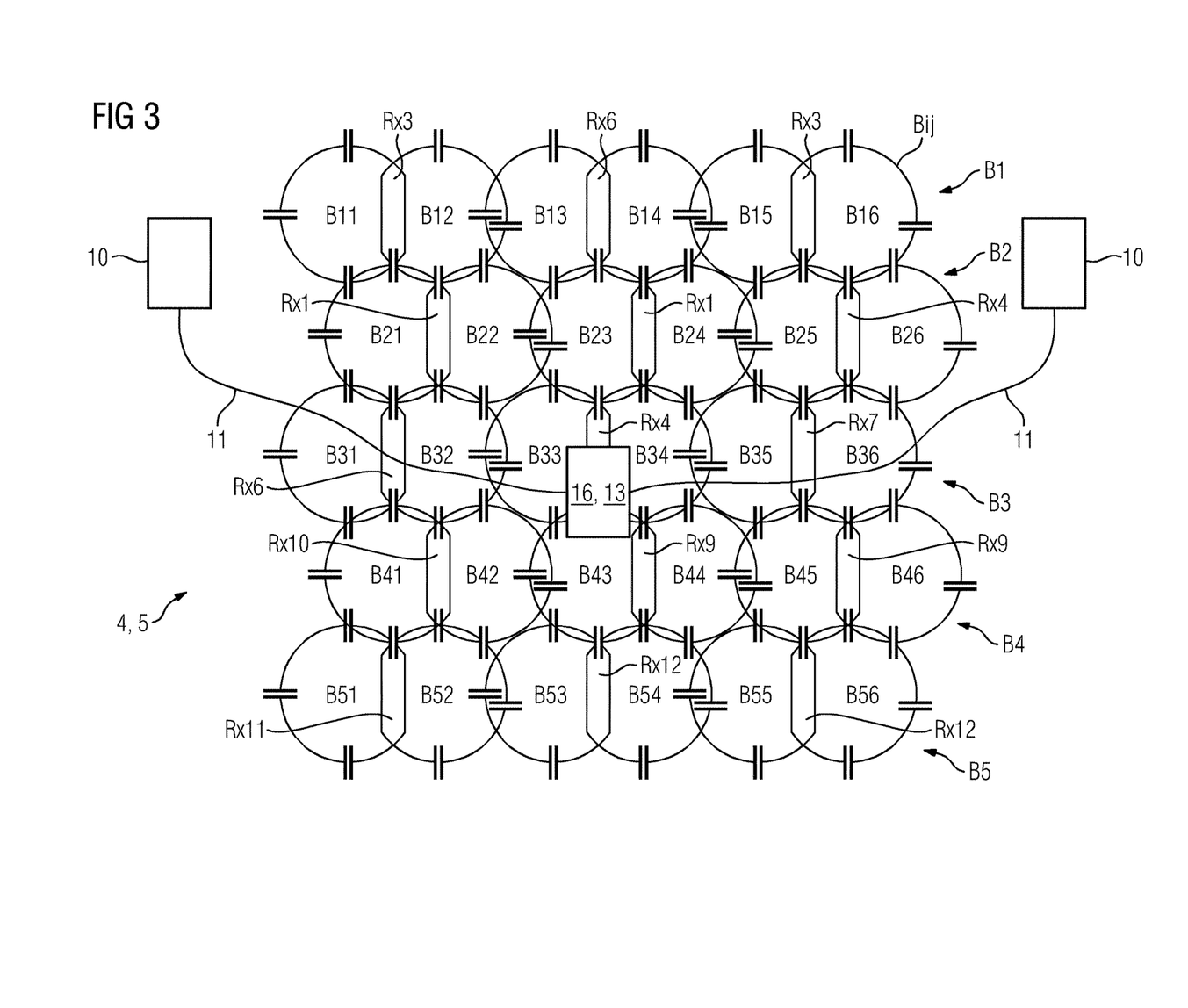
FIG. 3 depicts example coil elements of an MR coil.

FIG. 3 depicts the thirty (30) coil elements Bij arranged in the hexagonal 5×6 basic pattern or "array" (where i=1, . . . , 5 rows and j=1, . . . , 6 columns) of the two MR surface coils 4 and 5. Therefore, the coil elements Bij are arranged in five rows B1, . . . B5 with six coil elements each, wherein adjacent rows B1, B5 are each displaced by a half diameter of the coil elements Bij. The decoupling of the coil elements Bij may be provided by a geometric overlap. The size of the individual coil elements Bij is approximately 10×10 cm. At the same time, all the coil elements Bij have the same size and/or shape. The provision of the 30-channel MR surface coil 4 or 5 makes it possible to increase the so-called PAT factor by way of a higher number of receiving coil elements Bij in the field-of-view, "FOV" and hence to reduce the measuring time and number of artifacts.

In each case, one common receiving electronics unit Rx is assigned to one pair of two adjacent coil elements Bij. The total of fifteen receiving electronics units Rx is connected to a central flat module 16 from which the cables 11 emerge. The flat module 16 further includes the memory 13 for storing the identification. To enable the large amount of data generated by the high number of coil elements Bij to be generated sufficiently quickly, two cables 11 and manual plug connectors 10 are used. The flat module 16 may also include one of the receiving electronics units Rx.

Figure 6:
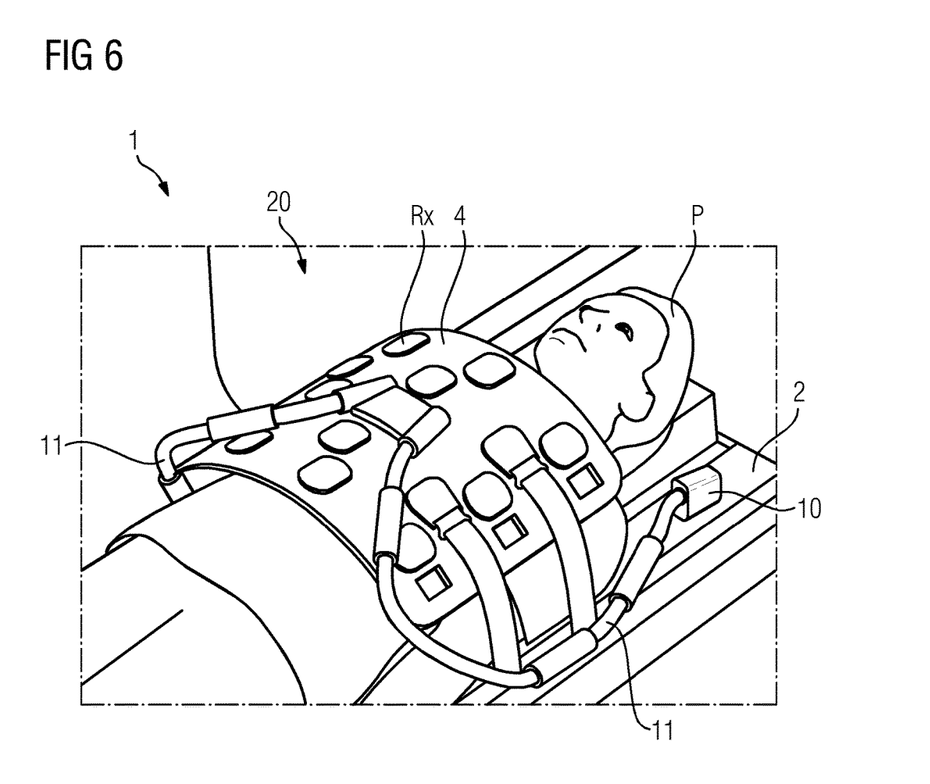
FIG. 6 depicts one embodiment of a MR System with a patient bed and an anteriorly attached MR coil.

The flat module 16 further includes a Hall sensor control (not shown) for position identification, for example 90°, 180° or 270° relative to a magnetic field direction of a B0 field of the body coil 20 (see FIG. 6).

To return once again to FIG. 2, the coil slide 15 here includes matching recesses for the receiving electronics units Rx and the flat module 16.

Figure 4:
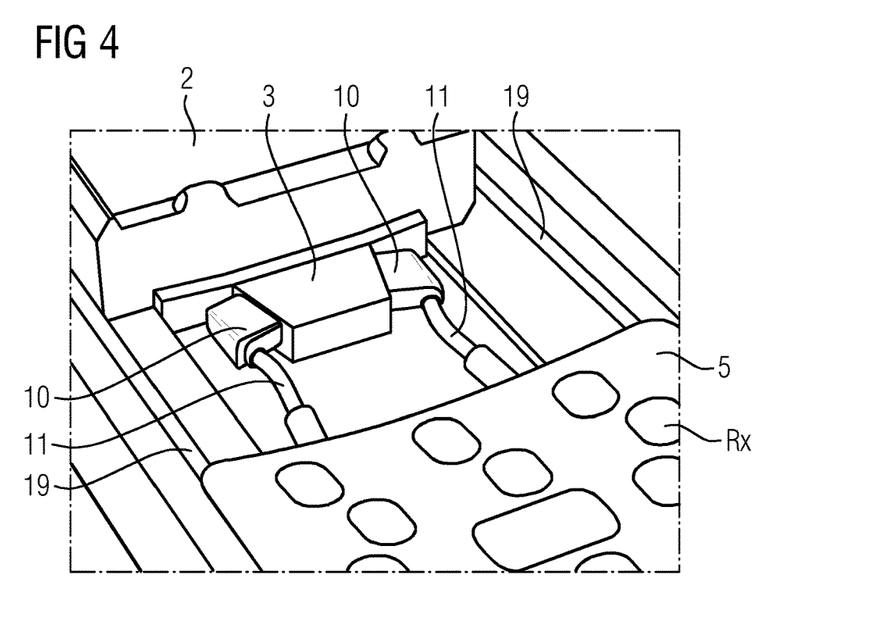
FIG. 4 depicts an embodiment of a patient bed with a posteriorly arranged MR surface coil.

FIG. 4 is an oblique top view showing the patient bed 2 with the posterior MR surface coil 5 lying on the coil slide 15 (not shown). Here, the coil slide 15 is mounted in slide guides 19 of the patient bed 2 so that the coil slide 15 may be displaced longitudinally or in the z direction. The accessory 3 is inserted in the patient bed 2, wherein the manual plug connectors 10 of the posterior MR surface coil 5 are inserted in the left-hand and right-hand sides of the accessory 3.

Figure 5:
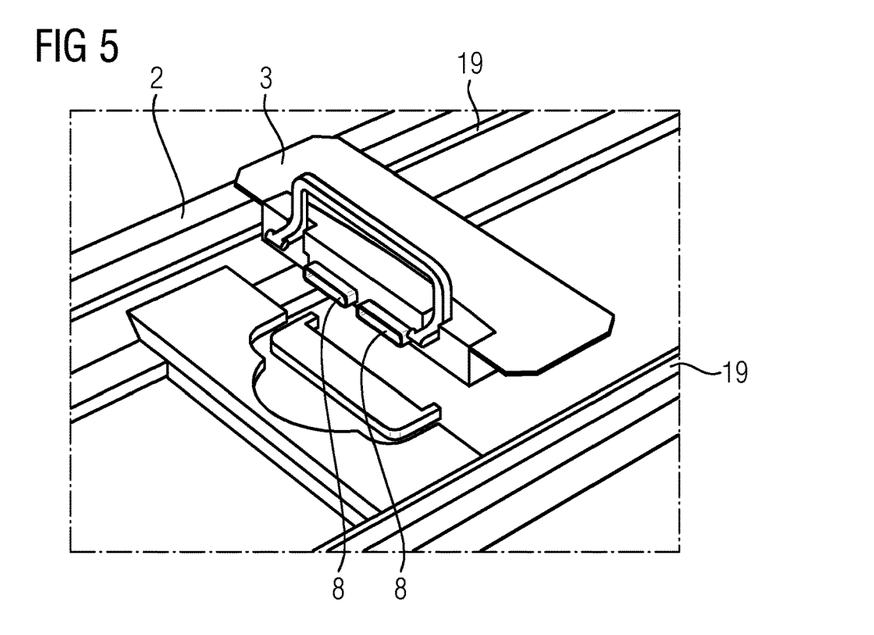
FIG. 5 depicts a patient bed with an accessory that has not yet been plugged in, according to one embodiment.

FIG. 5 is an oblique top view showing the patient bed 2 with an accessory 3 that has not yet been plugged in. The direct plug connectors 8 are inserted in the respective directly pluggable counter elements 14 (not shown) of the patient bed 2 in the longitudinal direction or z direction. The accessory 3 may then be interlocked on the patient bed 2.

FIG. 6 is an oblique top view showing the MR System 1 with the patient bed 2 and a whole body coil or MR tube 20 as components of the MR device 2, 20 and the anteriorly attached MR coil 4. The posteriorly attached MR coil 5 is either not shown or not present. Alternatively, it is possible with a posteriorly attached MR coil 5 to dispense with the anteriorly attached MR coil 4. The coil plugs 10 of the anteriorly attached MR coil 4 are inserted to the side of the patient P in the first device ports 12 (not shown).

Although the invention was illustrated and described in more detail by the exemplary embodiments, the invention is not restricted thereto and other variations may be derived herefrom by the person skilled in the art without departing from the scope of protection of the invention.

In general, "a", "one" etc. may be understood as meaning a singular or a plural in the sense of "at least one" or "one or more " etc., as long as this is not explicitly excluded, for example by the expression "exactly one" etc.

A numerical indication may also include the indicated number exactly and also a customary tolerance range, as long as this is not explicitly excluded.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:
1. A MR device comprising
a patient bed with at least one first device port for connecting an anteriorly positioned MR coil and at least one second device port for connecting a posteriorly positioned MR coil, wherein the at least one first device port is configured as a first type of port, and the at least one second device port is configured as a second type of port that is different than the first type of port;
a memory configured to store at least one set of coil file parameters for the anteriorly positioned MR coil and one set of coil file parameters for the posteriorly positioned MR coil; and
a processor configured to read an identification of the anteriorly positioned MR coil via the first device port and to read an identification of the posteriorly positioned MR coil via the second device port, the processor further configured to process MR signals originating from the anteriorly positioned MR coil by a set of coil file parameters that are selected on the basis of the identification read from the anteriorly positioned MR coil and the connection of the anteriorly positioned MR coil to the first device port, the processor further configured to process MR signals originating from the posteriorly positioned MR coil by a set of coil file parameters that are selected on the basis of the identification read from the posteriorly positioned MR coil and the connection of the posteriorly positioned MR coil to the second device port.

2. The MR device of claim 1, wherein the posteriorly positioned MR coil lies on a base that is variably positioned on the patient bed in the longitudinal direction of a patient.

3. The MR device of claim 2, further comprising:
a positioning cushion set with a plurality of segments inserted in series in the patient bed along a length of the bed.

4. The MR device of claim 1, further comprising:
a positioning cushion set with a plurality of segments inserted in series in the patient bed along a length of the bed.

5. The MR device of claim 1 further comprising
an at least one first accessory port that is connected to the at least one second device port,
wherein the posteriorly arranged MR coil is a surface coil with a plurality of coil elements and wherein an at least one coil port is connected to a second accessory port and wherein the anteriorly arranged MR coil has a same design as the posteriorly arranged MR coil and the at least one coil port is connected to the first device port.

6. The MR device of claim 5, wherein the MR coils are surface coils with a plurality of coil elements, that are positioned both anteriorly and posteriorly with respect to a patient.

7. The MR device of claim 6, wherein the MR coils each comprise two coil ports for connecting the coil elements.

8. The MR device of claim 5, wherein the MR coils each comprise two coil ports for connecting the coil elements.

9. A method for preparing an MR device, the method comprising:
connecting an at least one first accessory port to an at least one first device port of a patient bed of the MR device,
connecting an at least one coil port of an anteriorly arranged MR coil to a second device port of the MR device;
connecting an at least one coil port of a posteriorly arranged MR coil to a second accessory port;
reading associated identification from both the anteriorly arranged MR coil and the posteriorly arranged MR coil; and
processing MR signals originating from the MR coils using a respective set of coil file parameters, wherein the respective set of coil file parameters is selected based on the identification read from the respective MR coil and the connection of the respective MR coil to the respective device port.

* * * * *